(12) United States Patent
    Denyer et al.

(10) Patent No.:    US 12,623,031 B2
(45) Date of Patent:        May 12, 2026

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,383

(22) Filed: Aug. 29, 2024

(65) Prior Publication Data

US 2026/0061139 A1        Mar. 5, 2026

(51) Int. Cl.
    *A61M 5/32*        (2006.01)
(52) U.S. Cl.
    CPC ... *A61M 5/3243* (2013.01); *A61M 2005/3267* (2013.01)
(58) Field of Classification Search
    CPC ........ A61M 5/3243; A61M 2005/3247; A61M 5/3257; A61M 5/326; A61M 2005/3258; A61M 2005/3267; A61M 5/3275
    See application file for complete search history.

(56) References Cited

U.S. PATENT DOCUMENTS

| | | | |
|---|---|---|---|
| 4,118,611 A | 10/1978 | Harris | |
| 4,923,447 A | 5/1990 | Morgan | |
| 5,609,577 A * | 3/1997 | Haber ................. | A61M 5/3243 |
| | | | 604/110 |

(Continued)

FOREIGN PATENT DOCUMENTS

| | | |
|---|---|---|
| CA | 2645485 A1 | 9/2007 |
| JP | H06-15002 A | 1/1994 |

(Continued)

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

(Continued)

*Primary Examiner* — Emily L Schmidt
(74) *Attorney, Agent, or Firm* — Fish & Richardson P.C.

(57)                ABSTRACT

The present disclosure relates to a medicament delivery device. The medicament delivery device comprises a housing, a needle, and a needle cover. The needle cover is axially movable between an extended position and a retracted position. The medicament delivery device comprises a needle cover biasing member configured to bias the needle cover axially in the distal direction towards the extended position. The needle cover biasing member is configured to transition from a non-buckled state to a buckled state during proximal movement of the needle cover from the extended position to the retracted position. The present disclosure also relates to a method of preparing a medicament delivery device, and a method of locking a medicament delivery device.

14 Claims, 5 Drawing Sheets

(56) References Cited

U.S. PATENT DOCUMENTS

| | | | | |
|---|---|---|---|---|
| 5,743,888 A * | 4/1998 | Wilkes | ................ | A61M 5/3275 |
| | | | | 604/198 |
| 6,261,264 B1 * | 7/2001 | Tamaro | ............... | A61M 5/3271 |
| | | | | 128/919 |
| 9,192,731 B2 | 11/2015 | Roberts et al. | | |
| 10,765,811 B2 | 9/2020 | Vedrine et al. | | |
| 10,926,040 B2 | 2/2021 | Karasawa | | |
| 12,303,675 B1 | 5/2025 | Denyer et al. | | |
| 12,318,582 B1 | 6/2025 | Denyer et al. | | |
| 12,329,954 B1 | 6/2025 | Denyer et al. | | |
| 2004/0044318 A1 * | 3/2004 | Fiser | ................... | A61M 5/3275 |
| | | | | 604/263 |
| 2005/0171477 A1 * | 8/2005 | Rubin | ................ | A61M 5/2033 |
| | | | | 604/156 |
| 2011/0276029 A1 * | 11/2011 | Field | .................... | A61M 5/326 |
| | | | | 604/506 |
| 2012/0101475 A1 | 4/2012 | Wilmot et al. | | |
| 2014/0236094 A1 | 8/2014 | Riedel | | |
| 2016/0271319 A1 | 9/2016 | Bengtsson et al. | | |
| 2018/0200487 A1 * | 7/2018 | Sokolski | ............... | A61M 5/326 |
| 2019/0298924 A1 | 10/2019 | Gibson et al. | | |
| 2021/0128836 A1 | 5/2021 | Kiilerich | | |
| 2021/0308380 A1 | 10/2021 | Travanty et al. | | |
| 2022/0288318 A1 | 9/2022 | Plambech et al. | | |
| 2024/0198013 A1 | 6/2024 | Laurence et al. | | |

FOREIGN PATENT DOCUMENTS

| | | | |
|---|---|---|---|
| WO | WO 2009/079807 A1 | 7/2009 | |
| WO | WO 2025/188595 A1 | 9/2025 | |

OTHER PUBLICATIONS

Speciale et al., "Snap-Through Buckling Mechanism for Frequency-up Conversion in Piezoelectric Energy Harvesting," Applied Sciences, May 23, 2020, 10(10):3614, 18 pages.

U.S. Appl. No. 18/818,944, filed Aug. 29, 2024, Timothy Denyer.

U.S. Appl. No. 18/819,625, filed Aug. 29, 2024, Timothy Denyer.

U.S. Appl. No. 18/819,704, filed Aug. 29, 2024, Timothy Denyer.

International Search Report and Written Opinion in International Appln. No. PCT/US2025/030728, mailed on Jul. 8, 2025, 17 pages.

International Search Report and Written Opinion in International Appln. No. PCT/US2025/030731, mailed on Jul. 17, 2025, 17 pages.

International Search Report and Written Opinion in International Appln. No. PCT/US2025/028867, mailed on Sep. 4, 2025, 18 pages.

International Search Report and Written Opinion in International Appln. No. PCT/US2025/043341, mailed on Nov. 27, 2025, 17 pages.

* cited by examiner

500

550

511

501

570

551

506, 560

500

511

550

551

501

570

506, 560

MEDICAMENT DELIVERY DEVICE

TECHNICAL FIELD

This application relates to a medicament delivery device.

BACKGROUND

Medicament delivery devices are used to deliver a range of medicaments.

In some devices, the device must be held in a holding position at an injection site for a predetermined period of time, to ensure that the correct dose of medicament is dispensed from the device, before removing the device from the injection site.

It may be difficult to hold the device in the holding position whilst the medicament is dispensed. This may result in pain, discomfort, a wet injection site, early device removal and/or partial delivery of the medicament.

The present disclosure provides an improved medicament delivery device.

SUMMARY

According to a first aspect of the present disclosure, there is provided a medicament delivery device comprising a housing comprising a proximal end and a distal end, a needle and a needle cover, wherein the needle cover is axially movable between an extended position, in which the needle cover extends from the distal end of the housing and covers a distal end of the needle, and a retracted position, in which the needle cover is located in a proximal position relative to the extended position such that the needle protrudes from a distal end of the needle cover, a needle cover biasing member configured to bias the needle cover axially in the distal direction towards the extended position, wherein the needle cover biasing member is configured to transition from a non-buckled state to a buckled state during proximal movement of the needle cover from the extended position to the retracted position.

One advantage of the needle cover biasing member buckling when the needle cover biasing member is compressed during movement of the needle cover from the extended position to the retracted position is that the biasing force provided by the needle cover biasing member in its buckled state is reduced compared to the biasing force provided by the needle cover biasing member in its non-buckles state for the same displacement. Therefore, the force against which a user must hold the medicament delivery device during use is reduced. This may be particularly advantageous for users that lack strength to hold a medicament delivery device against the force of a needle cover biasing member for longer periods of time.

In some embodiments, the needle cover biasing member may be is configured to elastically buckle from the non-buckled state to the buckled state.

In some embodiments, when the needle cover is in the retracted position, the needle cover biasing member in the buckled state may be configured to provide a restoring force to move the needle cover to the extended state once a compressive force on the needle cover is removed.

Thus, the needle cover biasing member may return to its original unbuckled state. The return to the unbuckled state may allow the medicament delivery device to still be operated if the needle cover is accidentally moved proximally without insertion of the needle. Furthermore, the return of the needle cover biasing member to its unbuckled state when the compressive force on the needle cover is removed allows the needle cover to recover the needle to prevent accidental contact with the needle after use.

In some embodiments, the needle cover biasing member may be configured to transition to the buckled state once the needle cover has travelled over 50% of the distance from the extended position to the retracted position.

Thus, the medicament delivery device may be designed such that moving the needle cover proximally to insert the needle into an injection site may still require such force that accidental needle contact is not possible, and that the holding force required to counteract the needle cover biasing force is sufficiently reduced once the needle cover has travelled over 50% of the distance. The distance at which the needle cover biasing member moves to the buckling state may coincide with needle insertion. It will be appreciated, that in some embodiments, the needle cover biasing member may move to the buckled state when the needle cover has travelled over 40%, or over 30%, or over 20% of the distance from the extended position to the retracted position. The force profile required to insert the needle may be the same as in known devices and then less than known devices after the needle is inserted and the needle cover biasing member buckles.

In some embodiments, the needle cover may comprise a flange located proximate the distal end of the needle cover, the needle cover biasing member may be mounted on its distal end to the flange and the opposing proximal end may be mounted to a mount proximate the distal end of the housing.

Thus, the length of the needle cover biasing member, and thus diameter, of the needle cover biasing member can be kept relatively small. This reduces the size of the needle cover biasing member and space required in the medicament delivery device to house the needle cover biasing member. As a result, when the needle cover biasing member buckles, it is less likely to contact another component of the medicament delivery device or impede movement or function of the other components, i.e. allow unimpeded movement of the needle cover relative to the needle and medicament container.

In some embodiments, the needle cover biasing member may comprise a coil spring. In some embodiments, the coil spring may have a slenderness ratio of greater than or equal to 4. In some embodiments, the coil spring is configured to buckle when the deflection to free height ratio is between 0.25 and 0.65.

Thus, the properties of the needle cover biasing member may be tailored to cause transition from the unbuckled state to the buckled state at a predetermined deflection of the coil spring. Therefore, the force profile required to operate the medicament delivery device can be designed for use by specific demographics or based upon travel distance of the needle cover required before the reduction in force.

In some embodiments, the needle cover biasing member may be is a flat strip.

The flat strip may help to save space within needle cover of the medicament delivery device and may also provide higher forces at shorter deflection heights.

In some embodiments, the medicament delivery device may further comprise a needle cover biasing member compartment configured to house the needle cover biasing member and an axially movable compression member, the needle cover biasing member may be mounted on a distal end to the compression member and may be mounted on the proximal end to a mount of the housing.

Thus, the needle cover biasing member may be housed in an isolated compartment so that no other components or systems of the medicament delivery device can interact with the needle cover biasing member and compression member except for the needle cover.

In some embodiments, the needle cover biasing member may be mounted centrally in the needle cover biasing member compartment such that the needle cover biasing member extends coincidentally with the longitudinal axis of the medicament delivery device when in its unbuckled state.

Thus, the needle cover biasing member has an even amount of space to buckle into on all sides of the needle cover biasing member compartment.

In some embodiments, the needle cover biasing member compartment may be located at the proximal end of the housing.

Thus, the needle cover biasing member compartment is proximally located of all the other components in the housing. Therefore, the needle cover biasing member mechanism does not inhibit movement of function of any of the other components in the housing. This allows the design of the other components and systems to remain simple and/or the same as in known devices without large modifications.

In some embodiments, the needle cover may comprise a proximally extending arm configured to engage the distal surface of the compression member, and movement of the needle cover from the extended position towards the retracted position may move the compression member proximally.

In some embodiments, the needle cover biasing member compartment may comprise a compression member engaging element projecting radially inwards, the compression member engaging element configured to inhibit axial movement of one side of the compression member to trigger the transition of the needle cover biasing member from its non-buckled state to its buckle state.

Thus, the exact distance that the needle cover travels in the proximal direction before the needle cover biasing member is moved from its buckled to its buckled state can be predetermined.

In some embodiments, the needle cover biasing member may be located radially inwards of the outer surface of the needle cover.

Thus, the needle cover biasing member cannot be tampered with from outside of the medicament delivery device. The placement also helps to ensure that the function of the needle cover biasing member is not affected by the outside environment, such as physical contact, environmental conditions, or detritus.

In some embodiments, the medicament delivery device may be configured to inject greater than 2 ml of medicament and/or wherein the medicament delivery device is configured to inject medicament having a viscosity of greater than 25 cP.

In some embodiments, the medicament delivery device may further comprise a needle cover lock configured to prevent proximal movement of the needle cover once the needle cover is in the extended position post-use.

Therefore, after use, the needle cover may permanently cover the needle to prevent an accidental contact with the used needle.

In some embodiments, the medicament delivery device may comprise medicament.

The medicament delivery device may comprise a container for containing the medicament. The medicament may be located in the container. The container may be a syringe. The syringe may comprise the needle. The container may be a cartridge which is initially separated from the needle when the needle cover is in the extended position.

In a second aspect of the present disclosure, there is provided a method of preparing a medicament delivery device for use, the method comprising moving a needle cover in a proximal direction from an extended position, in which the needle cover extends from a distal end of a housing and covers a distal end of a needle, to a retracted position, in which the needle cover is located in a proximal position relative to the extended position such that the needle protrudes from a distal end of the needle cover, to compress a needle cover biasing member, and causing the needle cover biasing member to transition to a buckled state to reduce the hold force required for subsequent use of the medicament delivery device.

In a third aspect of the present disclosure, there is provided a method of locking a medicament delivery device after medicament has been dispensed from the medicament delivery device, the method comprising moving a needle cover in a distal direction from a retracted position, in which a needle protrudes from a distal end of the needle cover, to an extended position, in which the needle cover extends from a distal end of a housing and covers a distal end of the needle, under the restoring force of a needle cover biasing member in a buckled state, extending the needle cover such that the needle cover biasing member moves into its unbuckled state, and engaging a needle cover lock to prevent proximal movement of the needle cover.

BRIEF DESCRIPTION OF THE FIGURES

Embodiments will now be described, by way of example only, with reference to the accompanying drawings, in which.

DETAILED DESCRIPTION

Figure 1A:
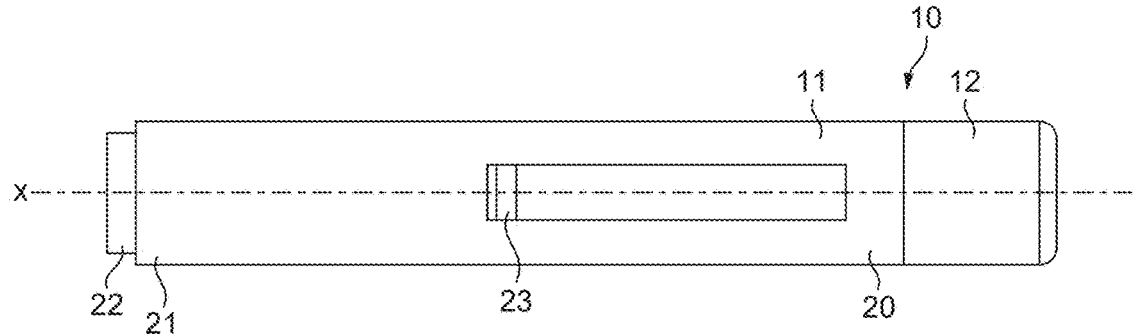
FIG. 1A shows an injector device with a cap attached.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
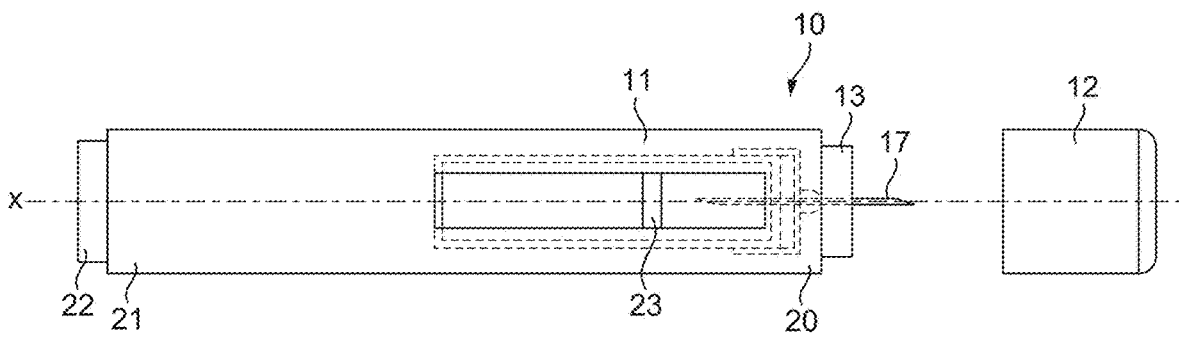
FIG. 1B shows the injector device of FIG. 1A with the cap removed.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23.

Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11. Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
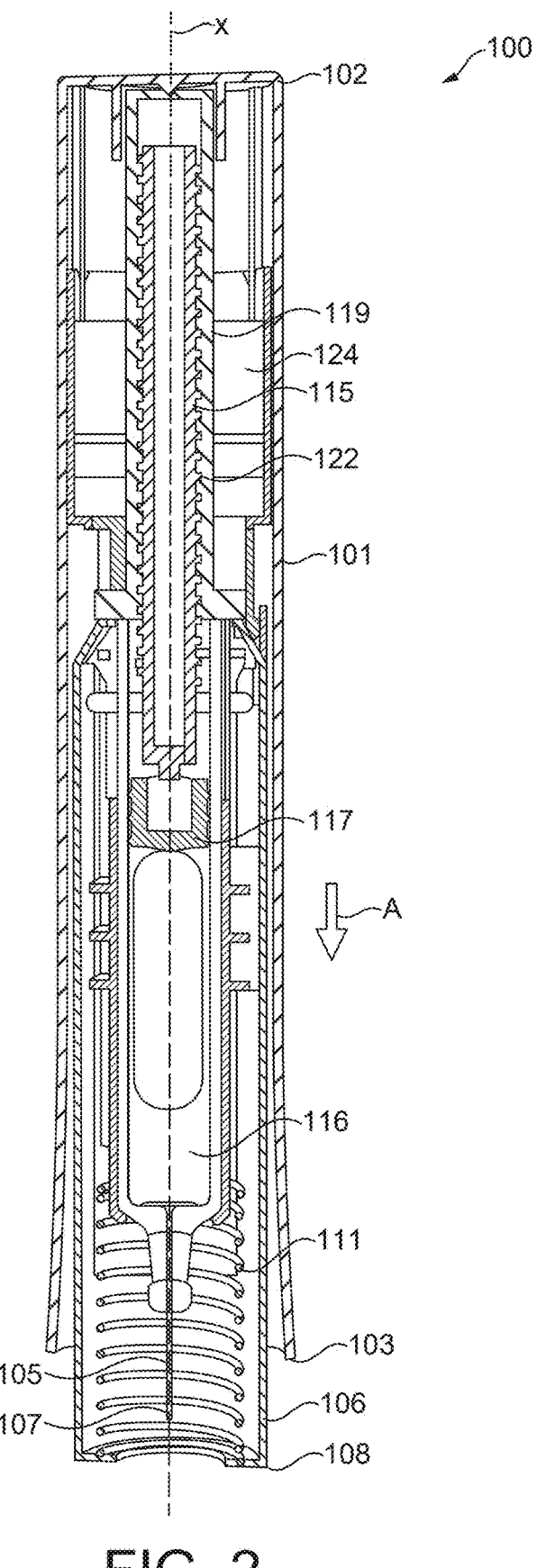
FIG. 2 shows a simplified schematic cross-sectional side view of a medicament delivery device.

FIG. 2 shows a simplified view of a medicament delivery device 100. The medicament delivery device 100 comprises a housing 101. The housing 101 comprises a proximal end 102 and a distal end 103. The medicament delivery device 101 further comprises a needle 105 for injecting medicament and a needle cover 106. The needle 105 has a distal end 107. The needle cover 106 is axially movable relative to the housing 101 between an extended position, in which the needle cover 106 extends from the distal end 103 of the housing 101 and covers the distal end 107 of the needle 105, and a retracted position, in which the needle cover 106 is located in a proximal position relative to the extend position such that the needle 105 protrudes from a distal end 108 of the needle cover 106. The medicament delivery device 100 extends along an axis X.

The medicament delivery device 100 is shown in the extended position in FIG. 2. The extended position may be the initial position in which the medicament delivery device 100 is provided.

The medicament delivery device 100 further comprises a needle cover biasing member 111. The needle cover biasing member 111 is configured to bias the needle cover 106 axially in the distal direction towards the extended position. The distal direction is indicated by the direction of the arrow A in FIG. 2. In some embodiments, the needle cover biasing member 111 may be a spring.

The medicament delivery device 100 may further comprise a plunger rod 115. The plunger rod 115 may be axially moveable within the housing 101. The medicament delivery device 100 may further comprise a syringe 116. The syringe 116 may be configured to contain medicament. The syringe 116 may comprise the needle 105 located on a distal end of the syringe 116. The plunger rod 115 may be axially movable within a syringe 116 of the medicament delivery device 100 to dispense medicament from the syringe 116 via the needle 105. The syringe 116 may comprise a piston 117. The plunger rod 115 may act on the piston to dispense medicament from the syringe 116 via the needle 105.

The medicament delivery device 100 may further comprise a collar 119. The collar 119 may be axially fixed relative to the housing 101. The collar 119 may interfaces with the plunger rod 115 via a screw thread 122. The medicament delivery device 100 may further comprise a drive member 124. The drive member 124 may be a biasing member that is configured to rotate the collar 119 when the drive member 124 is released. The drive member 124 may be a rotational biasing member, such as a spring. The spring 124 may be a torsion spring. The torsion spring 124 may be released when the needle cover 106 reaches a predetermined axial displacement in the proximal direction with a release mechanism (not shown). The rotation of the collar 119 may cause the plunger rod 115 to move distally within the syringe 116, in view of the screw thread 122, to thereby dispense medicament from the syringe 116 via the needle 105.

The needle cover 106 may be moved axially into the housing 101 uncovering the needle 105. The needle cover 106 may be moved proximally by being pressed against an injection site. The proximal axial displacement of the needle cover 106 may cause the release of the spring 124 which rotates the collar 119. The rotation of the collar 119 may move the plunger rod 115 axially in the distal direction within the syringe 116 to dispense the medicament via the needle 105.

The medicament delivery device 100 may be pressed against the injection site, to hold the needle cover 106 in the retracted position whilst the medicament is dispensed from the medicament delivery device 100. In known medicament delivery devices, the user must hold the medicament delivery device 100 against the injection site against the force of the needle cover biasing member 111.

After the medicament has been dispensed, the medicament delivery device 100 is removed from the injection site. The needle cover 106 may move distally under the force of the needle cover biasing member 111 to a locked position. In the locked position, the needle cover 106 covers the distal end 107 of the needle 105. In the locked position, the needle cover 106 may be prevented from moving proximally.

The medicament delivery device 100 may be configured to inject greater than 2 ml of medicament and/or the medicament delivery device 100 is configured to inject medicament having a viscosity of greater than 25 cP.

Figure 3:
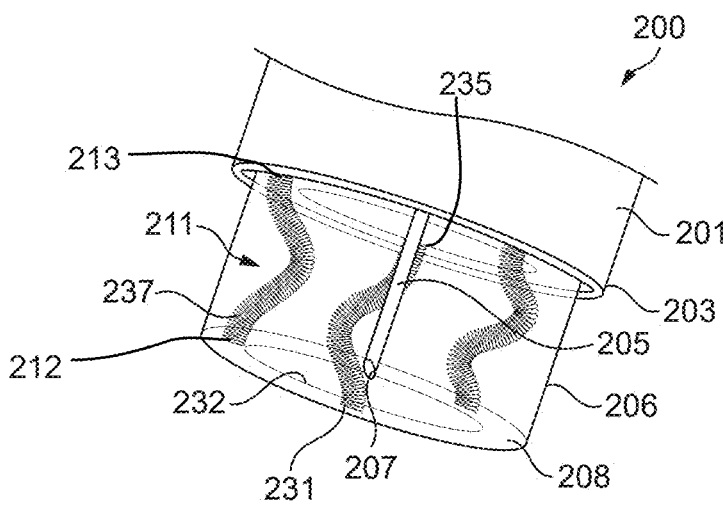
FIG. 3 shows a schematic perspective view of a distal end of a medicament delivery device when a needle cover is in an extended position.

FIG. 3 shows a schematic perspective view of a distal end of a medicament delivery device 200. The features described and/or contemplated in relation to the medicament delivery device 200 may be incorporated in the medicament delivery device 100 described and/or contemplated above. Furthermore, similar features and components will retain the same terminology and the reference numerals will be similar but having been increased in value by 100.

FIG. 3 shows a medicament delivery device 200. The medicament delivery device 200 comprises a housing 201. The housing 201 comprises a proximal end (not shown) and a distal end 203. The medicament delivery device 200 further comprises a needle 205 and a needle cover 206. The needle cover 206 is axially movable between an extended position and a retracted position. It will be appreciated that FIG. 3 illustrates the medicament delivery device 200 in a position somewhere between the extended position and the retracted position.

In the extended position, the needle cover 206 extends from the distal end 203 of the housing 201 and covers a distal end 207 of the needle 205. In the retracted position, the needle cover 206 is located in a proximal position relative to the extend position. In the retracted position, the needle cover is proximally located such that the needle 205 protrudes from a distal end 208 of the needle cover 206.

The medicament delivery device 200 further comprises a needle cover biasing member 211. The needle cover biasing member 211 is configured to bias the needle cover axially in the distal direction towards the extended position. Furthermore, the needle cover biasing member 211 is configured to transition from a non-buckled state to a buckled state during proximal movement of the needle cover 206 from extended position to the retracted position.

One advantage of the needle cover biasing member 211 buckling when the needle cover biasing member 211 is compressed during movement of the needle cover 206 from the extended position to the retracted position is that the biasing force provided by the needle cover biasing member 211 in its buckled state is reduced compared to the biasing force provided by the needle cover biasing member 211 in its non-buckles state for the same displacement. Therefore, the force against which a user must hold the medicament delivery device 200 during use is reduced. This may be particularly advantageous for users that lack strength to hold a medicament delivery device against the force of a needle cover biasing member for longer periods of time.

The needle cover biasing member 211 may be configured to elastically buckle from the non-buckled state to the buckled state. In some embodiments, when the needle cover 206 is in the retracted position, the needle cover biasing member 211 may be configured to provide a restoring force to move the needle cover 206 to the extended state once a compressive force on the needle cover 206 is removed. As a result, the needle cover biasing member 211 may return from the buckled state to the non-buckled state once the proximal force is removed from the needle cover 106. Therefore, once the medicament delivery device 200 is removed from the injection site, the needle cover biasing member 211 may provide the required force to extend the needle cover 206 from the retracted position to the extended position to cover the needle 205.

It will be appreciated that in an alternative embodiment, the needle cover biasing member 211 may be configured to plastically buckle, such that the needle cover biasing member 211 cannot provide a restoring force to move the needle cover 206 from the retracted position to the extended position. In such embodiments, the medicament delivery device 200 may further comprise a needle cover restoring member configured to distally move the needle cover from the retracted position to the extended position after the medicament delivery device 200 has been used. One advantage of a plastically buckling of the needle cover biasing member 211 is that the holding force required by the user can be eliminated.

As illustrated in FIG. 3, in some embodiments, the housing 201 of the medicament delivery device 201 may be generally cylindrical having an open distal end 203 through which the needle cover 206 is moveable. The housing 201 may be generally annular. That is, the housing 201 may be hollow. The needle cover 206 may be located radially inward of the housing 201. The needle cover 206 may also be generally cylindrical having an open distal end 208 such that the needle 205 may extend from the needle cover 206 when the needle cover 206 is in the retracted position. The needle cover 206 may be generally annular. That is, the needle cover 206 may be hollow.

In some embodiments, the needle cover 206 may comprise a flange 231. The flange 231 may be located proximate to the distal end 208 of the needle cover 206. In some embodiments, the flange 231 may be located at the distal end 208 of the needle cover 206. The flange 231 may extend circumferentially about the open distal end 208 of the needle cover 206. The flange 231 may extend radially inward from the distal end 208 of the needle cover 206. In some embodiments, the flange 231 may extend perpendicularly to the axis X of the medicament delivery device 200. Thus, the flange 231 may increase the contact area of the needle cover 206 with an injection site, which may make the operation of the medicament delivery device 200 more pleasant for the patient.

As shown in FIG. 3, the needle cover biasing member 211 may be mounted on its distal end 212 to the flange 231. The needle cover biasing member 211 may be mounted on a proximal facing surface 232 of the flange 231. Thus, the needle cover biasing member 211 is located inwardly of the needle cover 206. That is, the needle cover biasing member 211 may be located radially inwards of an outer surface of the needle cover 206. The needle cover biasing member 211 may be mounted on its opposing proximal end 213 to a mount 235 proximate to the distal end 203 of the housing 201.

In some embodiments, the mount 235 may be located at the same radial distance from the central longitudinal axis X of the medicament delivery device 200 as the mounting point of the needle cover biasing member 211 on the flange 231. In some embodiments, the mount 235 and the mounting point of the needle cover biasing member 211 on the flange 231 may be circumferentially aligned. Therefore, the needle cover biasing member 211 may extend parallel to the longitudinal axis X of the medicament delivery device 200 when the needle cover biasing member 211 is in its non-buckled state.

It will be appreciated that in some embodiments, the mount 235 may be located at a different radial distance from the central longitudinal axis X of the medicament delivery device 200 to the mounting point of the needle cover biasing member 211 on the flange 231. In addition or alternatively, it will be appreciated that in some embodiments, the mount 235 and the mounting point of the needle cover biasing member 211 on the flange 231 may be circumferentially offset. Therefore, the needle cover biasing member 211 may extend at an inclined angle to the longitudinal axis X of the medicament delivery device 200 when the needle cover biasing member 211 is in its non-buckled state.

Some of the advantages of inclining extension direction of the needle cover biasing member 211 to the direction of movement of the needle cover 206 include that the onset of the buckled state can be tuned to occur earlier than when the compression direction of the spring is the same as the direction of movement of the needle cover 206 for the same needle cover biasing member 211, and the direction of buckling can be controlled.

As shown in FIG. 3, when the needle cover 206 is moved proximally from the extended position towards the retracted position, the needle cover biasing member 211 may be compressed. The needle cover biasing member 211 may be compressed between the flange 231 of the needle cover 206 and the mount 235 of the housing 201. As the needle cover 206 is moved closer to the retracted position, the needle cover biasing member 211 may be further compressed. The needle cover biasing member 211 may be compressed substantially in the axial direction until it is compressed by a critical distance. Once the needle cover biasing member 211 is compressed beyond the critical distance, the needle cover biasing member 211 may move from its non-buckled state to its buckled state.

In some embodiments, the needle cover biasing member 211 may be configured to transition from the non-buckled state to the buckled state once the needle cover 206 has travelled over 50% of the distance from the extended position to the retracted position. One advantage of the needle cover biasing member 211 buckling after the needle cover 206 has travelled over 50% of the needle cover stroke, i.e. distance between extended and retracted positions, is that the force required to expose the needle 205 remains high to aid in preventing accidental needle contact.

In other embodiments, the distance that the needle cover 206 may cover before the needle cover biasing member 211 transitions from the non-buckled state to the buckled state may vary. For example, in some embodiments, the needle cover biasing member 211 may be configured to transition from the non-buckled state to the buckled state once the needle cover 206 has travelled over 40%, or over 30%, or over 20% of the needle cover stroke.

In some embodiments, the medicament delivery device 200 may comprise a plurality of needle cover biasing members 211. The plurality of needle cover biasing members 211 may be circumferentially spaced about the longitudinal axis X of the medicament delivery device 200. That is, the plurality of biasing members 211 may be circumferentially spaced about the flange 231 of the needle cover 206 and the mount 235 on the housing 201. The plurality of needle cover biasing members 211 may be equidistantly spaced about the longitudinal axis, i.e. along the proximal facing surface 232 of the flange 231.

One of the advantages of using a plurality of needle cover biasing members 211 includes being able to use biasing members 211 having smaller cross-sectional dimensions. Needle cover biasing members 211 having smaller cross-sectional dimensions in a plane transverse to their longitudinal dimension take up less space in the cavity inside the needle cover 206 and move from the non-buckled state to the buckled state in a shorter distance than a needle cover biasing member 206 of the same length with larger cross-sectional dimensions.

Each of the plurality of needle cover biasing members 211 may be identical. Therefore, each of the plurality of needle cover biasing members 211 may be configured to transition from the non-buckled state to the buckled state after the same distance of compression. Thus, the plurality of needle cover biasing members 211 are able to provide a balanced reaction force to the compression force at each point between the extended position and the retracted position of the needle cover 206. This enables smooth axial movement of the needle cover 206 between the extended position and the retracted position, i.e. without twisting moments.

In some embodiments, the needle cover biasing member 211 may comprise a coil spring 237, as shown in FIG. 3. The medicament delivery device 200 may comprise a plurality of coil springs 237, as shown in FIG. 3.

A number of factors determine when a spring, such as a coiled spring 237, will transition from a non-buckled state to a buckled state. These factors include the slenderness ratio of the spring, the number of coils in the spring, and the wire diameter, i.e. width, as well as the properties of the material that forms the spring and the end conditions, i.e. how the spring is mounted.

The slenderness ratio of the spring is the ratio of the free length, i.e. non-compressed length, of the spring divided by the mean diameter of the spring, i.e. average of the outer and inner diameters of a coil. The larger the slenderness ratio of a spring, the more likely it is to buckle for a given compression distance, i.e. deflection. In other words, springs with a larger slenderness ratio can be deflected less before they buckle than springs with smaller slenderness ratios.

In some embodiments, the coil spring 237 may have a slenderness ratio of greater than or equal to 4. In some embodiments, the coil spring 237 may have a slenderness ratio of greater than or equal to 5. In some embodiments, the coil spring 237 may have a slenderness ratio of greater than or equal to 6. In some embodiments, the coil spring 237 may be configured to buckle when the deflection to free height ratio is between 0.25 and 0.65.

In some embodiments, the medicament delivery device 200 may further comprise a needle cover lock. The needle cover lock may be configured to prevent proximal movement of the needle cover once the needle cover 206 is returned to the extended position post-use. The needle cover lock may be of any known configuration.

Figure 4:
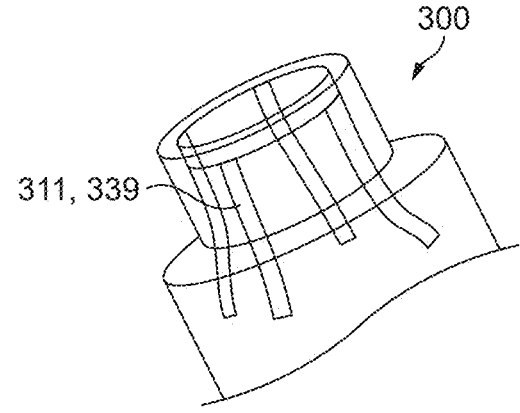
FIG. 4 shows a schematic perspective view of a distal end of a medicament delivery device when a needle cover has been moved proximally from an extended position.

Referring now to FIG. 4, a schematic perspective view of a distal end of a medicament delivery device 300 is shown.

The medicament delivery device 300 of FIG. 4 is generally the same as the medicament delivery device 200 as described previously in relation to FIG. 3. Therefore, a detailed description of the medicament delivery device 300 will be omitted for the sake of brevity. Furthermore, similar features and components will retain the same terminology and reference numerals.

The main difference between the medicament delivery device 300 shown in FIG. 4 and the medicament delivery device 200 shown in FIG. 3, is that the needle cover biasing member 311 of the medicament delivery device 300 shown in FIG. 4 comprises a flat strip 339. As shown in FIG. 4, the medicament delivery device 300 may comprises a plurality of flat strips 339.

Figure 5:
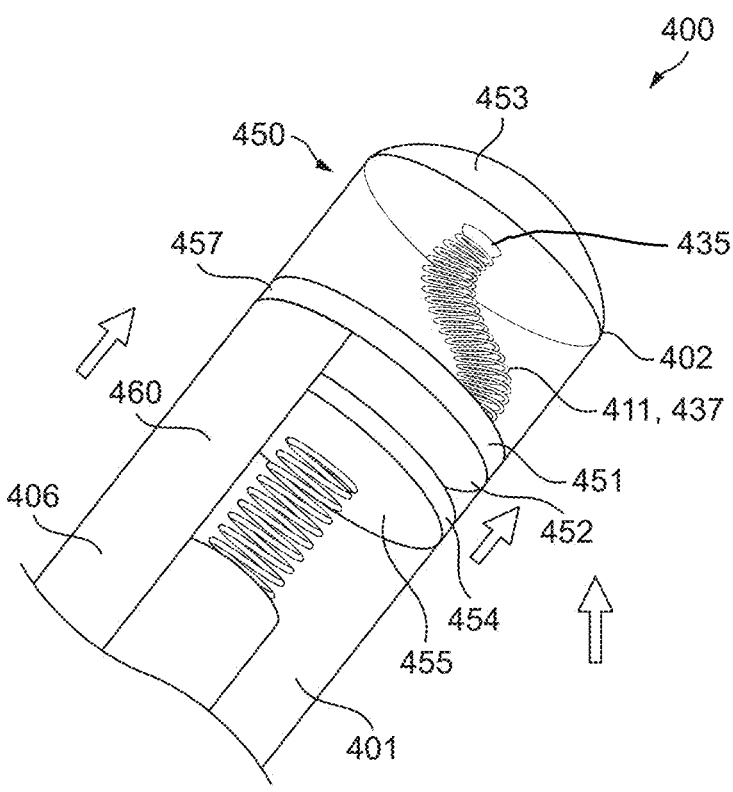
FIG. 5 shows a schematic perspective view of a proximal end of a medicament delivery device when a needle cover has been moved proximally from an extended position.
Figure 6:
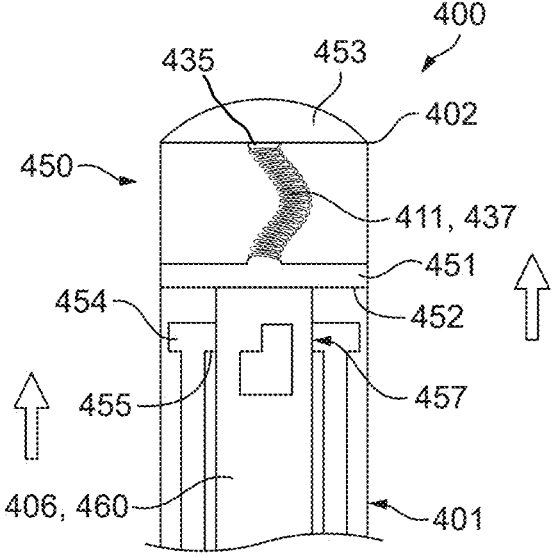
FIG. 6 shows a simplified schematic side view of a proximal end of a medicament delivery device when a needle cover has been moved proximally from an extended position.

Referring now to FIG. 5 and FIG. 6, schematic perspective and side views of a proximal end of a medicament delivery device 400 are shown. The medicament delivery device 400 of FIG. 5 and FIG. 6 is generally the same as the medicament delivery device 200 as described previously in relation to FIG. 3. Therefore, a detailed description of the medicament delivery device 400 will be omitted for the sake of brevity. Furthermore, similar features and components will retain the same terminology and the reference numerals will be similar but having been increased in value by 200 relative to the medicament delivery device 200 described in relation to FIG. 3.

FIGS. 5 and 6 show a medicament delivery device 400. The medicament delivery device 400 comprises a housing 401. The housing 401 comprises a proximal end 402 and a distal end (not shown). The medicament delivery device 200 further comprises a needle (not shown in FIG. 5 or FIG. 6) and a needle cover 406. The needle cover 406 is axially moveable between an extended position and a retracted position, shown in FIGS. 5 and 6.

In the extended position, the needle cover 406 extends from a distal end (not shown) of the housing 402 and covers a distal end of the needle. In the retracted position, the needle cover 406 is located in a proximal position relative to the extended position. In the retracted position, the needle cover 406 is proximally located such that the needle protrudes form a distal end (not shown) of the needle cover 406.

The medicament delivery device 400 further comprises a needle cover biasing member 411. The needle cover biasing member 411 is configured to bias the needle cover 406 axially in the distal direction towards the extended position. Furthermore, the needle cover biasing member 411 is configured to transition from a non-buckled state to a buckles state, as shown in FIGS. 5 and 6, during proximal movement of the needle cover 406 from the extended position to the retracted position. As previously explained, buckling of the needle cover biasing member reduces the force against which an operator must hold the medicament delivery device 400 during use.

The needle cover biasing member 411 may be configured to elastically buckle from the non-buckled state to the buckled state. In some embodiments, when the needle cover 406 is in the retracted position, the needle cover biasing member 411 in the buckled state may be configured to provide a restoring force to bias the needle cover 406 towards the extended state once a compressive force on the needle cover 406 is removed. Therefore, once the medicament delivery device 400 is removed from the injection site, the needle cover biasing member 411 may provide the required force to extend the needle cover 406 from the retracted position to the extended position to cover the needle.

As illustrated in FIG. 5, in some embodiments, the housing 401 of the medicament delivery device 401 may be generally cylindrical. The housing 401 may be generally annular. That is, the housing 401 may be hollow. The needle cover 406 may be located radially inward of the housing 402. The needle cover 406 may also be generally cylindrical having an open distal end, as shown in the embodiment illustrated in FIG. 2. The needle cover 206 may be generally annular. That is, the needle cover 406 may be hollow.

The medicament delivery device 400 may further comprise a needle cover biasing member compartment 450. The needle cover biasing member compartment 450 may be configured to house the needle cover biasing member 411. The needle cover biasing member compartment 450 may comprise a compression member 451. The compression member 451 may be axially moveable within the needle cover biasing member compartment 450. In some embodiments, the compression member 451 may be a flat plate. In some embodiments, the compression member 451 may be a circular plate.

As shown in FIGS. 5 and 6, the needle cover biasing member compartment 451 may be located at the proximal end 402 of the housing 401. Thus, the needle cover biasing member compartment 451 may be defined on its proximal end by an end cap 453. The end cap 453 may close the proximal end 402 of the housing 401. The end cap 453 may be integrally formed with the housing 401.

The needle cover biasing member compartment 451 may be defined on its distal end by structural element 454. The structural element 454 may be a transversely extending element. The structural element 454 may provide a rigid support of the housing 402 for other mechanisms to be biased against. For example, as shown in FIG. 5, a plunger rod 415 may be biased distally by a drive member 424 mounted on its proximal end on a distal facing surface 455 of the structural element 454.

In some embodiments, the structural element 454 may be configured to provide at least one gap between the edge of the structural element 454 and the inner surface of the housing 401. In some embodiments, the structural element 454 may comprise an aperture 457 extending therethrough. In some embodiments, the aperture 457 may be located on the periphery of the structural element 454 to provide a gap between the structural element 454 and the inner surface of the housing 401. The side wall of the needle cover biasing member compartment 450 may be defined by the inner surface of the housing 401.

As shown in FIGS. 5 and 6, the needle cover biasing member 411 may be mounted on a distal end to the compression member 451. The needle over biasing member 411 may also be mounted on its proximal end to a mount 435 on the housing 401. The mount 435 on the housing 401 may be located on the distally facing surface of the end cap 453. The needle cover biasing member 411 may be mounted centrally in the needle cover biasing member compartment 450 such that the needle cover biasing member 411 extends coincidentally with the longitudinal axis of the medicament delivery device 400 when the needle cover biasing member 411 is in its unbuckled state. In some embodiments, the needle cover biasing member 411 may be mounted off-centre in the needle cover biasing member compartment 450.

The needle cover 406 may comprise a proximally extending arm 460. The proximally extending arm 460 may be configured to engage a distally facing surface 452 of the compression member 451. The proximally extending arm 460 may be configured to engage the distally facing surface of the compression member 451 when the needle cover 406 is in its extended position. Therefore, the needle cover 406 cannot be accidentally moved in the proximal direction. The aperture 457 in the structural element 454 may be configured to allow the arm 460 of the needle cover 406 to move axially therethrough.

Movement of the needle cover 406 in the proximal direction from the extended position towards the retracted position may cause the arm 460 of the needle cover 406 to bias the compression member 451 in the proximal direction. As the compression member 451 moves proximally, the compression member 451 compresses the needle cover biasing member 411. Once the compression member 451 has moved by a predetermined distance, the deflection of the needle cover biasing member 411 passes its critical value and the needle cover biasing member 411 moves from its non-buckled state to it buckled state reducing the holding force required to be provided by the user.

In some embodiments, the needle cover 406 may only comprise a single arm 460 configured to engage with the compression member 451, as shown in FIGS. 5 and 6. One advantage of such an arrangement is that the force is transferred to the needle cover biasing member asymmetrically, i.e. with rotation inducing moments. Therefore, the compression member 451 may rotate within the needle cover biasing member compartment 450 and the transition of the needle cover biasing member 411 from the non-buckled state to the buckled state may occur earlier.

Alternatively, in some embodiments, the needle cover 406 may comprise a plurality of arms 460 configured to engage with the compression member 451. The plurality of arms 460 may be spaced equidistantly about the longitudinal axis X of the medicament delivery device 400. One advantage of such an arrangement is that the force is transferred to the needle cover biasing member 411 symmetrically, i.e. without rotation inducing moments. Therefore, the transition of the needle cover biasing member 411 from the non-buckled state to the buckled state can be controlled solely by the needle cover biasing member 411 geometry, i.e. slenderness ratio. In the symmetrical arrangement, the compression member 451 may comprise a plurality of tabs (not shown) configured to be located in channels (not shown) in the inner surface of the housing 401 configured to prevent the compression member 451 from rotating during movement of the needle cover 406 between extended and retracted positions.

In some embodiments, the needle cover biasing member 411 may comprise a coil spring 437, as shown in FIGS. 5 and 6. In some embodiments, the medicament delivery device 400 may comprise a plurality of coil springs 437.

Figure 7:
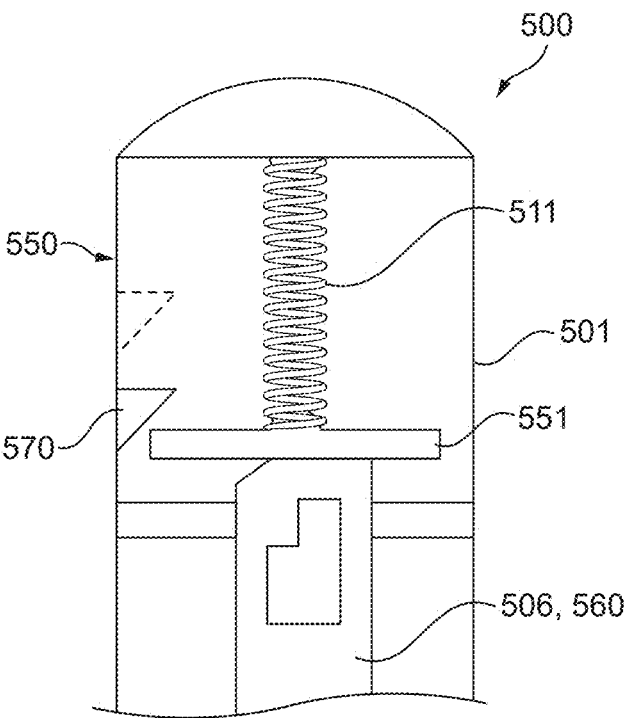
FIG. 7 shows a simplified schematic side view of a proximal end of a medicament delivery device when a needle cover is in an extended position.
Figure 8:
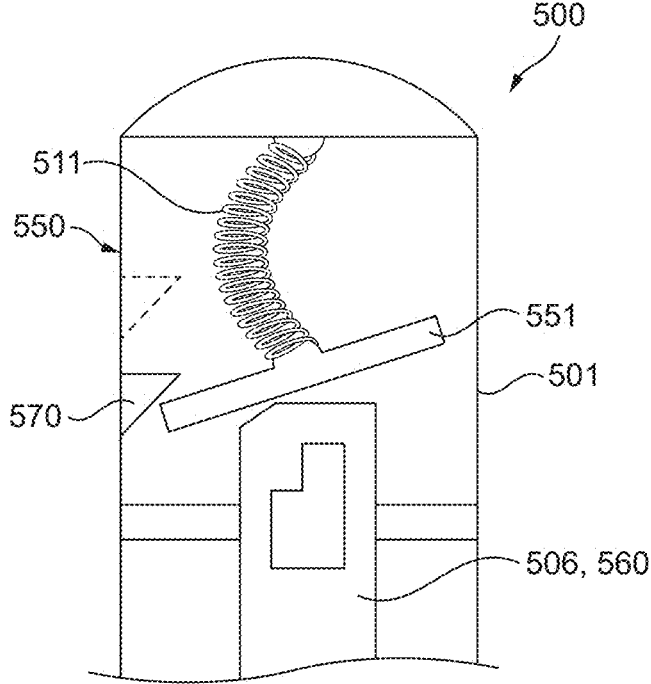
FIG. 8 shows a simplified schematic side view of a proximal end of the medicament delivery device in FIG. 7 when the needle cover has been moved proximally from an extended position.

Referring now to FIGS. 7 and 8, schematic perspective and side views of a proximal end of a medicament delivery device 500 are shown. The medicament delivery device 500 of FIG. 7 and FIG. 8 is generally the same as the medicament delivery device 400 as described previously in relation to FIG. 5 and FIG. 6. Therefore, a detailed description of the medicament delivery device 500 will be omitted for the sake of brevity. Furthermore, similar features and components will retain the same terminology and the reference numerals will be similar but having been increased in value by 100 relative to the medicament delivery device 400 described in relation to FIGS. 5 and 6.

The main difference between the medicament delivery device 500 shown in FIGS. 7 and 8 and the medicament delivery device 400 shown in FIGS. 5 and 6, is that the needle cover biasing member compartment 550 of the medicament delivery device 500 shown in FIGS. 7 and 8 may further comprise a compression member engaging element 570.

The compression member engaging element 570 may project radially inwards into the needle cover biasing member compartment 550. In some embodiments, the compression member engaging element 570 may extend inwardly from the inner surface of the housing 501 forming the side wall of the needle cover biasing member compartment 550. The compression member engaging element 570 may be configured to inhibit axial movement of one side of the compression member 551. Therefore, the compression member engaging element 570 may be configured to trigger the transition of the needle cover biasing member 511 from its non-buckled state to its buckled state, as shown in FIGS. 7 and 8. One advantage of such an arrangement is that a stronger needle biasing member 511 may be used compared to an arrangement without the engaging element because the mechanism does not have to rely solely on the needle cover biasing member's properties or characteristics but is physically manipulated into the buckled state.

The compression member engaging element 570 may be circumferentially spaced from the at least one arm 560 of the needle cover 506. This allows the compression member 551 to be rotated without inhibiting movement of the needle cover 506. The compression member engaging element 570 may take any suitable shape. For example, as shown in FIGS. 7 and 8 the compression member engaging element 570 may be triangular.

In some embodiments, at least a portion of the compression member 551 may remain in contact with the compression member engaging element 570 once the needle cover biasing member 511 has transitioned from the non-buckled state to the buckled state. That is, at least a portion of the compression member 551 may be located distally of the compression member engaging element 570 when the needle cover 506 is in its retracted position. Therefore, the compression member 551 does not fully pass the compression member engaging element 570. As a result, the needle cover biasing member 511 does not have to overcome the compression member engaging element 570 to return the needle cover from the retracted position to the extended position once the hold force is removed. However, it will be appreciated that in some embodiments, the entire compression member 551 may be located proximally of the compression member engaging element 570 when the needle cover 506 is in the retracted position.

The compression member engaging element 570 may be axially located within the needle cover biasing member compartment 550 at a position configured to cause the needle cover biasing member 511 to transition from the non-buckled state to the buckled state once the needle cover 506 has travelled at least 50% of the distance from the extended position to the retracted position. That is, the compression member engaging element 570 may be located axially midway along the needle cover biasing member compartment 550.

In other embodiments, the compression member engaging element 570 may be located at an axial position dependent upon the preferred reduction of the holding force required to operate the medicament delivery device 500. For example, the compression member engaging element 570 may be located at an axial distance from the distal end of the needle cover biasing member compartment 550 in the range of 20% to 70% the length of the compartment 550.

Although described previously in detail, a brief description of the method of preparing a medicament delivery device for use will be described hereinafter. The method of preparing a medicament delivery device comprises moving a needle cover in a proximal direction from an extended position to a retracted position to compress a needle cover biasing member. The method further comprises causing the needle cover biasing member to transition to a buckled state to reduce the hold force required for subsequent use of the medicament delivery device.

In some embodiments, the method may comprise compressing the needle cover biasing member beyond its critical deflection such that the needle cover biasing member to transitions to its buckled state. In some embodiments, the method may comprise inducing a compressive force on the needle cover biasing member that is misaligned with the longitudinal axis of the needle cover biasing member to trigger transition of the needle cover biasing member to its buckled state.

The medicament delivery device may also be locked after medicament has been dispensed from the medicament delivery device. The method of locking the device comprises moving a needle cover in a distal direction from a retracted position to an extended position under the restoring force of a needle cover biasing member in a buckled state. The method further comprises extending the needle cover under the force of the needle cover biasing member such that the needle cover biasing member moves into its unbuckled state, and engaging a needle cover lock to prevent proximal movement of the needle cover.

The features described and/or contemplated in relation to the medicament delivery device 200, 300, 400, 500 may be incorporated in another medicament delivery device, for example a medicament delivery device having a different mechanism for dispensing medicament to that described in relation to the medicament delivery device 100, and/or a medicament delivery device which is configured to inject 2 ml or less of medicament and/or a medicament delivery device which is configured to inject medicament having a viscosity of 25 cP or less, and/or a medicament delivery device in which the medicament is contained in a cartridge which is initially separated from the needle when the needle cover is in the initial position.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N—(ω-carboxyheptadecanoyl)-des(B30) human insulin and B29-N—(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a caperturesterol-reducing antisense therapeutic for the treatment of familial hyper-caperturesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

REFERENCE NUMERALS

10 Medicament Delivery Device
11 Housing
12 Cap Assembly
13 Needle Sleeve
17 Needle
20 Distal Region
21 Proximal Region
22 Button
23 Piston
100 Medicament Delivery Device
101 Housing
102 Proximal End
103 Distal End
105 Needle
106 Needle Cover
107 Distal End
108 Distal End
111 Needle Cover Biasing Member
115 Plunger
116 Syringe
117 Piston
119 Collar
122 Screw Thread
124 Drive Member
125 Injection Site
200 Medicament Delivery Device
201 Housing
203 Distal End
205 Needle
206 Needle Cover
207 Distal End
208 Distal End
211 Needle Cove Biasing Member
231 Flange

232 Proximal Facing Surface
235 Mount
237 Coil Spring
300 Medicament Delivery Device
311 Needle Cover Biasing Member
339 Flat Strip
400 Medicament Delivery Device
401 Housing
402 Proximal End
406 Needle Cover
411 Needle Cover Biasing Member
437 Coil Spring
450 Needle Cover Biasing Member Compartment
451 Compression Member
452 Distally Facing Surface
453 End Cap
454 Structural Element
455 Distally Facing Surface
457 Aperture
460 Arm
500 Medicament Delivery Device
501 Housing
506 Needle Cover
511 Needle Cover Biasing Member
550 Needle Cover Biasing Member Compartment
551 Compression Member
560 Arm
570 Compression Member Engaging Element
X Central Longitudinal Axis

The invention claimed is:

1. A medicament delivery device comprising:
a housing comprising a proximal end and a distal end;
a needle and a needle cover,
    wherein the needle cover is axially movable between an extended position, in which the needle cover extends from the distal end of the housing and covers a distal end of the needle, and a retracted position, in which the needle cover is located in a proximal position relative to the extended position such that the needle protrudes from a distal end of the needle cover; and
a needle cover biasing member configured to bias the needle cover axially in a distal direction towards the extended position, wherein the needle cover biasing member is located within the needle cover,
wherein the needle cover biasing member is configured to transition from a non-buckled state to a buckled state during proximal movement of the needle cover from the extended position to the retracted position, wherein when the needle cover biasing member is compressed yet before the needle cover biasing member has transitioned from the non-buckled state into the buckled state, the needle cover biasing member is arranged substantially along an axis, wherein the axis is defined by a first end of the needle cover biasing member and a second end of the needle cover biasing member that is opposite to the first end, and the axis is parallel to and radially outward from a longitudinal axis of the needle.

2. The medicament delivery device according to claim 1, wherein the needle cover biasing member is configured to elastically buckle from the non-buckled state to the buckled state.

3. The medicament delivery device according to claim 2, wherein when the needle cover is in the retracted position, the needle cover biasing member in the buckled state is configured to provide a restoring force to move the needle cover to the extended position once a compressive force on the needle cover is removed.

4. The medicament delivery device according to claim 1, wherein the needle cover biasing member is configured to transition to the buckled state once the needle cover has travelled over 50% of a distance from the extended position to the retracted position.

5. The medicament delivery device according to claim 1, wherein the needle cover comprises a flange located proximate the distal end of the needle cover, a distal end of the needle cover biasing member being mounted to the flange and the a proximal end of the needle cover biasing member being mounted to a mount proximate the distal end of the housing.

6. The medicament delivery device according to claim 1, wherein the needle cover biasing member comprises a coil spring.

7. The medicament delivery device according to claim 6, wherein the coil spring has a slenderness ratio of greater than or equal to 4.

8. The medicament delivery device according to claim 6, wherein the coil spring is configured to buckle when a deflection of the coil spring to free height ratio is between 0.25 and 0.65.

9. The medicament delivery device according to claim 1, wherein the needle cover biasing member is located radially inwards of an outer surface of the needle cover.

10. The medicament delivery device according to claim 1, wherein the medicament delivery device is configured to inject greater than 2 ml of a medicament and/or wherein the medicament delivery device is configured to inject a medicament having a viscosity of greater than 25 cP.

11. The medicament delivery device according to claim 1, wherein the medicament delivery device is configured to prevent the proximal movement of the needle cover once the needle cover is in the extended position post-use.

12. The medicament delivery device according to claim 1, wherein the medicament delivery device comprises a medicament.

13. A method of preparing a medicament delivery device for use, the method comprising:
moving a needle cover in a proximal direction from an extended position, in which the needle cover extends from a distal end of a housing and covers a distal end of a needle, to a retracted position, in which the needle cover is located in a proximal position relative to the extended position such that the needle protrudes from a distal end of the needle cover, to compress a needle cover biasing member located within the needle cover, and
causing the needle cover biasing member to transition to a buckled state to reduce a hold force required for counteracting a restoring force of the needle cover biasing member,
wherein when the needle cover biasing member is compressed yet before the needle cover biasing member has transitioned from a non-buckled state into the buckled state, the needle cover biasing member is arranged substantially along an axis, wherein the axis is defined by a first end of the needle cover biasing member and a second end of the needle cover biasing member that is opposite to the first end, and the axis is parallel to and radially outward from a longitudinal axis of the needle.

14. A method of locking a medicament delivery device after medicament has been dispensed from the medicament delivery device, the method comprising:
moving a needle cover in a distal direction from a retracted position, in which a needle protrudes from a distal end of the needle cover, to an extended position, in which the needle cover extends from a distal end of a housing and covers a distal end of the needle, under a restoring force of a needle cover biasing member in a buckled state, wherein the needle cover biasing member is located within the needle cover, extending the needle cover such that the needle cover biasing member moves into a non-buckled state, and preventing proximal movement of the needle cover once the needle cover is in the extended position post-use, wherein when the needle cover biasing member is compressed yet before the needle cover biasing member has transitioned from the non-buckled state to the buckled state, the needle cover biasing member is arranged substantially along an axis, wherein the axis is defined by a first end of the needle cover biasing member and a second end of the needle cover biasing member that is opposite to the first end, and the axis is parallel to and radially outward from a longitudinal axis of the needle.

\* \* \* \* \*